United States Patent [19]

White et al.

[11] Patent Number: 4,536,389

[45] Date of Patent: Aug. 20, 1985

[54] BACTERICIDAL TABLETTING COMPOSITION AND TABLETS FORMED THEREFROM

[75] Inventors: Christopher D. White, Richmond; Alan A. Levy, Stanmore, both of England

[73] Assignee: Richardson-Vicks Ltd., Egham, England

[21] Appl. No.: 533,762

[22] Filed: Sep. 19, 1983

[30] Foreign Application Priority Data

Oct. 12, 1982 [EP] European Pat. Off. ........ 82109431.5

[51] Int. Cl.$^3$ .............................................. A61K 9/46
[52] U.S. Cl. ...................................................... 424/44
[58] Field of Search .......................................... 424/44

[56] References Cited

U.S. PATENT DOCUMENTS

| | | | |
|---|---|---|---|
| 3,136,692 | 6/1964 | Bandelin | 424/44 |
| 3,495,001 | 2/1970 | Leonards | 424/44 |
| 3,653,914 | 4/1972 | Schmitt | 424/44 |

FOREIGN PATENT DOCUMENTS

| | | | |
|---|---|---|---|
| 55-7246 | 1/1980 | Japan | 424/44 |
| 1427710 | 3/1976 | United Kingdom | 424/44 |

OTHER PUBLICATIONS

Ball et al., C.A. 85 #51783v, (1976), of Brit. 1,427,710 Mar. 10, 1976.
Yamashita, C.A. 79 #139650m (1973) of Jpn. Koka 73 52919, Jul. 25, 1973.
Firth, C.A. 75 #144007d, (1971) of Brit. 1,165,098, Jul. 28, 1971.
Kirby, C.A. 93 #53967x, (1980) of Jpn. Tokkyo Koho 79 44,722, Sep. 24, 1969.
Firth, C.A. 73 #38549f, (1970) of S. African 69,04,056, Dec. 12, 1969.
Baker, C.A. 74 #115900p (1971) of Brit. 1,221,038, Feb. 3, 1971.

*Primary Examiner*—Shep K. Rose
*Attorney, Agent, or Firm*—George W. Rauchfuss, Jr.; Salvatore R. Conte

[57] ABSTRACT

Bactericidal tablets are formed from compositions containing dichloroisocyanurate and carbonate compounds without the necessity for a lubricant by employing powdered succinic acid of a specified particle size.

4 Claims, No Drawings

BACTERICIDAL TABLETTING COMPOSITION AND TABLETS FORMED THEREFROM

FIELD OF THE INVENTION

This invention relates to a novel bleaching, disinfecting, bactericidal and sterilizing tablet and more particularly to a tablet of this type which contains dichloroisocyanurate and carbonate components and which tablet must be quickly dissolved in water with effervescent evolution of carbon dioxide and release of available chloride. The invention relates most specifically to such a tablet that can be prepared without the use of a lubricant.

BACKGROUND OF THE INVENTION

For a number of reasons including package and dosage considerations it is highly desirable to be able to form a bleaching, disinfecting, bactericidal and sterilizing formulation such as that just immediately described hereinbefore into tablet form. For the most part it has not been heretofore possible to form such a formulation into tablet form except with the use of a lubricant in the composition because the resulting tablet has been uncompressible due to the most part to adhesion to punches or dies. It is highly desirable to be able to form a tablet from such a formulation without the necessity for a costly and undesirable lubricant. Heretofore it has only been disclosed that such a tablet could be prepared by employing adipic acid as the organic acid component of such a formulation, see British Pat. No. 1,165,098 of H. T. Kirby & Co., Limited.

SUMMARY OF THE INVENTION

It has now unexpectedly been discovered that such a tablet can be produced without the necessity for the use of a lubricant component if succinic acid of a particle size within a specified critical range is employed as the organic acid component of the formulation. More particularly, such a suitably stable tablet can be formed without the necessity for using a lubricant if one employs succinic acid powder having a particle size such as no more than 2% weight is retained on a 400 micron mesh screen and no more than 25% weight fines (particles less than 100 microns) are present in the succinic acid powder.

DETAILS OF THE INVENTION

It has now been discovered that a suitably stable bactericidal tablet as described hereinbefore can be produced from a formulation comprising the following components:
dichloroisocyanuric acid or alkali metal salt thereof: 10–40% weight
carbonate as alkali metal bicarbonate or mixtures of alkali metal, bicarbonates and carbonate: 20–50% weight
succinic acid powder: 20–50% weight
and wherein the succinic acid powder is of a particle size such that a maximum of 2% weight is retained on a 400 micron screen and no more than 25% weight passes through a 100 micron screen. Most preferably the succinic acid particle size is characterized by the following ranges:
on 40 micron screen: 2% weight maximum
through a 400 micron screen but retained on a 200 micron screen: 20 to 80% weight
through a 200 micron screen but retained on a 100 micron screen: 10 to 50% weight
through a 100 micron screen: 4 to 25% weight Most preferably the succinic acid powder has a particle size such that about 95% weight is less than 300 microns.

More preferably, the carbonate component of the tablet formulation of this invention is a mixture of carbonate and bicarbonate, preferably the alkali metal salts thereof and most preferably a mixture of sodium bicarbonate and sodium carbonate. Also, the dichloroisocyanuric acid is preferably present as an alkali metal dichloroisocyanurate and most preferably as sodium dichloroisocyanurate. Thus, a preferred tablet formulation of this invention comprises:
sodium dichloroisocyanurate: 10–40% weight
sodium carbonate: 0–15% weight
sodium bicarbonate: 20–50% weight
succinic acid: 20–50% weight A most preferred tablet composition of this invention consists of the following:
sodium dichloroisocyanurate: 25% weight
sodium bicarbonate 35% weight
sodium carbonate: 5% weight
succinic acid: 35% weight Tablets of this invention may be formed by any suitable tablet forming technique. For example, the first step of the manufacture of the product comprises a blending operation which may, for example, be of either of the following two types:

(A) by adding together the bicarbonate and succinic acid in a suitable drier such as a fluid bed, tray or vacuum drier/mixer and drying for a suitable period of time, such as for one hour at 90° C., after which the dried powders are cooled and mixed with the remaining ingredients in any suitable powder mixer; or (B) if the moisture content is below about 0.3% weight simply mixing all the powders together using any suitable mixer designated for that purpose.

The mixed powder produced by either of the above or any suitable process may then be tabletted on either a rotary or a reciprocating tablet machine to give a tablet of the desired weight.

It is preferred to produce a tablet such that a solution thereof provides a concentration of at least about 100 p.p.m. of available chlorine. For five liters of solution such a tablet of the most prefered composition of this invention would weigh about 3.2 grams.

Tablets of this invention are characterized by the tabletting machine being able to produce a tablet of smooth faces in the case of a reciprocating machine and in the case of a rotary machine to give such a tablet product and not to produce overloading of the machine. This is able to be done with the compositions of this invention despite the fact that said compositions do not have a lubricant present. It is recognized, however, that if one so desired, they could add a lubricant to the compositions of this invention although such a lubricant is not required and is generally not desired.

It is surprising that the powdered succinic acid of this invention as described hereinbefore produces such an acceptable tablet since the substitution of succinic acid of different particle size does not produce such an acceptable tablet nor does the use of tartaric or citric acid in the place of succinic acid. Said latter acids and coarse succinic acid produce highly undesirable sticking of the tablet punch faces.

We claim:

1. A tablet formed without a lubricant comprising:
   dichloroisocyanuric acid or alkali metal salt thereof: 10–40% weight
   carbonate as alkali metal bicarbonate or a mixture of alkali metal bicarbonate and carbonate: 20–50% weight
   characterized in that the composition also has present 20 to 50% weight succinic acid powder having a particle size such that a maximum of 2% weight is retained on a 400 micron screen and no more than 25% weight passes through a 100 micron screen.

2. A tabletted composition according to claim 1 wherein the succinic acid powder is characterized by the following size ranges:
   on a 400 micron screen: 2% weight
   through a 400 micron screen but retained on a 200 micron screen: 20–80% weight
   through a 200 micron screen but retained on a 100 micron screen: 10–50% weight
   through a 100 micron screen: 4–25% weight.

3. A tabletted composition according to claim 1 wherein the components of the composition comprise:
   sodium dichloroisocyanurate: 10–40% weight
   sodium carbonate: 0–15% weight
   sodium bicarbonate: 20–50% weight
   succinic acid: 20–50% weight.

4. A tabletted composition according to claim 3 comprising:
   sodium dichloroisocyanurate: 25% weight
   sodium bicarbonate: 35% weight
   sodium carbonate: 5% weight
   succinic acid: 55% weight.

* * * * *